(12) United States Patent
Papaioannou et al.

(10) Patent No.: US 7,397,900 B2
(45) Date of Patent: Jul. 8, 2008

(54) MICRO BEAM COLLIMATOR FOR HIGH RESOLUTION XRD INVESTIGATIONS WITH CONVENTIONAL DIFFRACTOMETERS

(75) Inventors: Dimitrios Papaioannou, Eggenstein-Leopoldshafen (DE); José-Luis Spino, Weingarten (DE)

(73) Assignee: Euratom, Luxembourg (LU)

( * ) Notice: Subject to any disclaimer, the term of this patent is extended or adjusted under 35 U.S.C. 154(b) by 284 days.

(21) Appl. No.: 11/358,513

(22) Filed: Feb. 21, 2006

(65) Prior Publication Data

US 2008/0043923 A1 Feb. 21, 2008

Related U.S. Application Data

(63) Continuation of application No. 10/381,641, filed on Mar. 26, 2003, now abandoned.

(51) Int. Cl.
*G21K 1/02* (2006.01)
*G21K 1/04* (2006.01)
*G21N 23/20* (2006.01)

(52) U.S. Cl. .................. 378/147; 378/70; 378/150

(58) Field of Classification Search .............. 378/70, 378/84, 147–151, 156, 159
See application file for complete search history.

(56) References Cited

U.S. PATENT DOCUMENTS

| 4,263,510 A * | 4/1981 | Ciccarelli et al. ............. 378/46 |
| 5,001,737 A | 3/1991 | Lewis et al. |
| 5,682,415 A | 10/1997 | O'Hara |
| 5,684,857 A | 11/1997 | De Bokx |
| 5,772,903 A | 6/1998 | Hirsch |
| 6,438,209 B1 * | 8/2002 | Rossiger ................. 378/150 |

FOREIGN PATENT DOCUMENTS

| EP | 1 100 092 A2 | 5/2001 |
| JP | 02-271300 | 11/1990 |
| JP | 04-0131402 | 5/1992 |
| JP | 05-297195 | 11/1993 |
| JP | 06-294898 | 10/1994 |
| JP | 09-251098 | 9/1997 |

OTHER PUBLICATIONS

D. Bilderback, S.A. Hoffman and D. Thiel, Science, 263 (1994).

(Continued)

*Primary Examiner*—Irakli Kiknadze
(74) *Attorney, Agent, or Firm*—Head, Johnson & Kachigian

(57) ABSTRACT

A micro collimator for compressing X-ray beams for use in a X-ray diffractometer is described, wherein said collimator has a channel means for providing a channel guiding said X-ray beams, said channel having a channel entrance portion and a channel exit portion. The object of the invention is to provide a micro beam collimator capable of being used in a conventional X-ray diffractometer with the Bragg-Brentano geometry, so as to enable the characterisation of very small sample regions without need of very large radiation sources (synchrotron). For solving this technical problem it is proposed to form the channel means by two opposite, polished, oblong plate means made of or coated with a material selected from the group consisting of the heavyweight metals and materials having total reflection properties comparable to those of the heavyweight metals.

20 Claims, 14 Drawing Sheets

OTHER PUBLICATIONS

Naoki Yamamoto, Rev. Sci. Instrum., 67 (9), (1996).
P. Dhez, P. Chevallier, T.B. Lucatorto and C. Tarrio, Rev. Sci. Instrum., 70, (4), (1999).
D. H. Bilderback, D.J. Thiel, Rev. Sci. Instrum., 66 (2) (1995).
A. H. Compton and S.K. Allison, "X-rays in Theory and Experiment", D. Van Nostrand Company, Inc., (1935).
D. J. Thiel, D. H. Bilderback and A. Lewis, Rev. Sci., Instrum., 64 (10), (1993).
I. C. Noyan, P.-C. Wang, S. K. Kaldor, J.L. Jordan-Sweet and E. G. Liniger, Rev. Sci. Instrumen., 71 (5) (2000).
C. A. MacDonald, S. M. Owens and W. M. Gibson, J. Appl. Cryst., 32, 160-167, (1999).

* cited by examiner (a)

(b)

MICRO BEAM COLLIMATOR FOR HIGH RESOLUTION XRD INVESTIGATIONS WITH CONVENTIONAL DIFFRACTOMETERS

This is a continuation application of Ser. No. 10/381,641 filed on Mar. 26, 2003, now abandoned which was allowed by Notice of allowance dated Nov. 18, 2005. The sole purpose of the present filing is to supply copies of the background publications cited in the specification.

The present invention relates to a micro beam collimator for compressing X-ray beams for use in a X-ray diffractometer and a method of carrying out high resolution XRD studies by using the same.

Concentrators or condensers producing high intensity X-ray beams in the micrometer size are valuable tools in many industrial and scientific fields. Applications of microfocusing techniques are increasingly reported in metal refining, semiconductor and ceramic industry, as well as in biological and medical sciences [see prior art references 1, 2]. Also, use of micro beams in several types of techniques, such as diffraction, spectroscopy or microscopy, improves their resolution and increases their applicability in many individual cases [see prior art references 1, 2].

Constructively, hard X-ray micro beam formation is overwhelmed by many limitations and technical difficulties. Contrary to visible light, X-ray focusing optics can not be based on conventional lenses, since the refractive index n for the air/solid interface is slightly less than unity. Also, due to this property, an X-ray striking a plane smooth surface will be reflected only if the incident angle remains lower than a critical $\theta_c$ which is calculated in the simplified form to $\theta_c = (2\delta)^{1/2}$ and $\delta = (Ne^2\lambda^2 Z\rho/(2\pi mc^2 A)$, where N=Avogadro's number, e=electron charge, $\lambda$=wave length of radiation, Z=atomic number, $\rho$=material density, m=electron mass, c=velocity of light and A=atomic mass [see prior art references 3, 4]. Detailed description of these phenomena can be found in many fundamental physics books [see prior art references 5, 6] and so will not be mentioned further in this text.

Most approaches for parallel micro beam generation are then based on the multiple total reflection of X-rays, usually inside lead-glass capillaries [see prior art references 1-4, 7, 8]. Directing the source X-rays towards the capillary tube entrance, the incident beam may be compressed, as long as the angle of incidence for each reflection remains below the critical value $\theta_c$. For lead glass and X-ray photons of 8 KeV, $\theta_c$ does not exceed 3 mrad (0.17°) [see prior art-reference 9]. Practically, this means that a tapered (lead glass) capillary of about 10 cm length will be limited to an entrance opening of about 20-50 µm, if an output beam size of 3-11 µm is required [see prior art references 1, 7]. Hence only an extremely small amount of the incident radiation can be condensed, for which micro-beam experiments of this kind require high input X-ray intensities and are usually performed with high-energy synchrotron radiation sources.

Further, an important aspect taken into account is that XRD observations of polycrystalline materials using Bragg-Brentano diffractometers, only the grains oriented parallel to the sample surface and therefore coincident with the zero position of the apparatus contribute to the diffracted intensity. Since in solid materials the grain size is in general in the micrometer range, it is only by chance that favourably oriented grains are illuminated when using cross-sectional micro-beam from capillary tubes, such that in this case, not only the incident but also the diffracted intensity is very low.

Therefore, it is the object of the present invention to provide a micro beam collimator for compressing X-ray beams for use in a conventional X-ray diffractometer with the Bragg-Brentano geometry, so as to enable the characterisation of very small sample regions without the need of very large radiation sources (synchrotron).

This technical problem is solved by a micro beam collimator having the features of claim 1 and by a method having the features of claim 19. Further features of the present invention are disclosed in the subclaims.

A possibility of increasing the amount of radiation that can be condensed is to use reflecting materials with higher $\theta_c$, such that larger portion of the incident beam is intersected by the collimator. Ideal materials for such a purpose are the heavyweight metals with high electron density=$(Z \cdot \rho/A)$, where Z=atomic number, $\rho$=material density and A=atomic mass). In addition, metals exhibit higher mechanical strength than glass, allowing more stable and larger capillary-type constructions. Thus, the efficiency of the collimator can be increased, since the longer the capillary and the larger its inlet aperture, the bigger the amount of radiation that can be captured and compressed. These concepts have been considered and successfully applied in the present invention, which deals with a capillary type construction based on opposite polished, oblong reflecting plates made of or coated with a material selected from the group consisting of the heavyweight metals and materials having total reflection properties comparable to those of the heavyweight metals.

Preferably, the two plate means are fully made of one of the materials according to the present invention. However, it would be sufficient to only have a coating of the respective material on the surfaces of the two plate means which are facing each other thereby forming a channel for guiding X-ray beams. Preferably, Nickel, Wolfram or Platinum is selected for the plate means. Alternatively, other heavyweight metals or such materials having total reflection properties, in particular critical angles of total reflection, comparable to those of the heavyweight metals may be used. Examples for the latter materials are alloys from heavyweight metals.

Each of the two plate means can be made in a one-piece or integral manner. Alternatively, each of the oblong or elongated plates may be made of two or more plate sections which are connected at their end surfaces in an appropriate manner.

The micro beam collimator of the present invention produces micro beams having a line- or linear-shaped rectangular cross-section, thin enough in one direction such that fine structure changes can be detected on scanning the sample, but sufficiently long in the other direction such that the largest number of grains is exposed for diffraction. The invention is therefore particularly applicable to diffraction analyses of very thin but long sample regions, as those characteristic of unidirectional interface growth (e.g. oxide layers in tubes or metal plates), requiring a specific sample preparation.

The invention applies the total reflection principles preferably on two opposite, flexible, polished, oblong Nickel (Ni)-plates (mirrors) that condense or compress the primary radiation emitted by a 2 kW laboratory X-ray tube with normal focus (Cu-anode). The compression is mono-directional and takes place between the two flexible-Ni-mirrors, which form a narrow channel of variable longitudinal profile (for example convex or tapered). The variability of this profile is assured by the reduced thickness of the Ni plates (chosen as for example 1 mm), so that they are stable but flexible enough, allowing adjustments of the channel profile to be freely done by adequate spacers and screws.

Since the critical angle $\theta_c$ for Ni is 0.42°, i.e., 2.5 times higher than for lead glass, a large entrance opening of the channel (about 0.5 mm) is permitted. Nominal dimension of the channel entrance is therefore 0.5 mm×4 mm. At the other extreme, the channel exit portion is provided with a constant cross section of 30 μm×4000 μm along a distance of about 37 mm, such that a quasi-parallel output beam is produced.

To further stop oblique radiation, an anti-divergence diaphragm (beam stopper) of 15 μm is placed at the channel exit. The output or compressed beam has therefore final norminal dimensions 15 μm×4000 μm, with measured intensity two orders of magnitude higher than an uncompressed beam with same dimensions.

Due to this high brilliance, the micro beam collimator can be operated in combination with common X-ray diffractometers to perform high-resolution structure analysis of very-thin but long solid layers or interfaces. This special kind of sample geometry appears in several technical materials applications, like in the rim region of longitudinally cut nuclear fuel pellets, oxide layers on metal plates, bonding layers in metal sheet-sandwiches, bonding layers in double-wall tubes, etc.

To ensure safe handling, according to the present invention, the two plates are contained in a preferably cylindrical housing- or holding means, preferably made of aluminium, mounted in a double-axis micro-positioning stage that is attached to the radiation tube housing. This construction allows easy alignment of the micro beam collimator with respect to the source beam.

Summarizing the present invention a micro beam collimator has been developed for condensing hard X-rays, providing very thin but intense low divergent beams. The primary radiation is compressed down to the micrometer size scale by multiple total reflections on the polished inner surfaces of a flat metallic channel of adjustable longitudinal profile. The obtained beam at the exit aperture has nominal dimensions of for example 15 μm×4000 μm (linear-shape cross section) and is two orders of magnitude more intense than the uncompressed radiation going through a slit of the same size. Owing to this high brilliance win, the collimator can be operated even with the conventional radiation tube of a common diffractometer. A prototype, being mounted on a commercial theta-theta diffractometer, has been thoroughly tested for intensity gain, divergence and spatial resolution. Thus, acquisition of accurate XRD patterns on oblong but very thin (only some tens of microns) sample regions has been easily carried out in the laboratory, without need of expensive high energy (sychnchrotron) radiation sources, as demanded in the most approaches of micro beams formation based on glass capillaries.

One embodiment of the present invention is described by means of the attached drawings and by example only. In the drawings.

Figure 1:
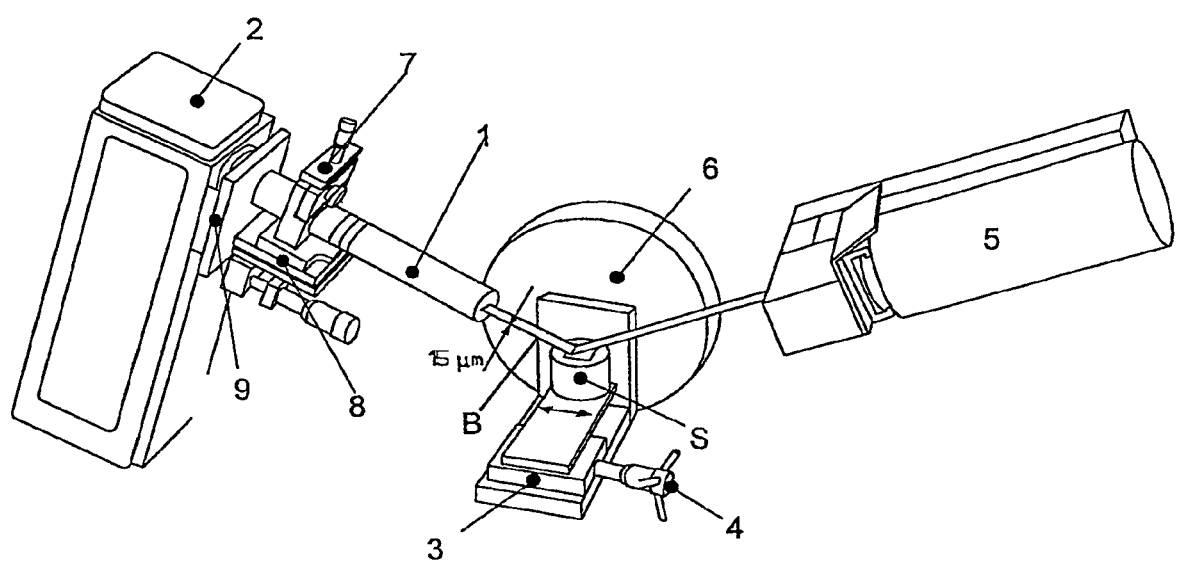
FIG. 1 is an perspective view showing schematically an X-ray apparatus employing the micro beam collimator according to the present invention.
Figure 5:
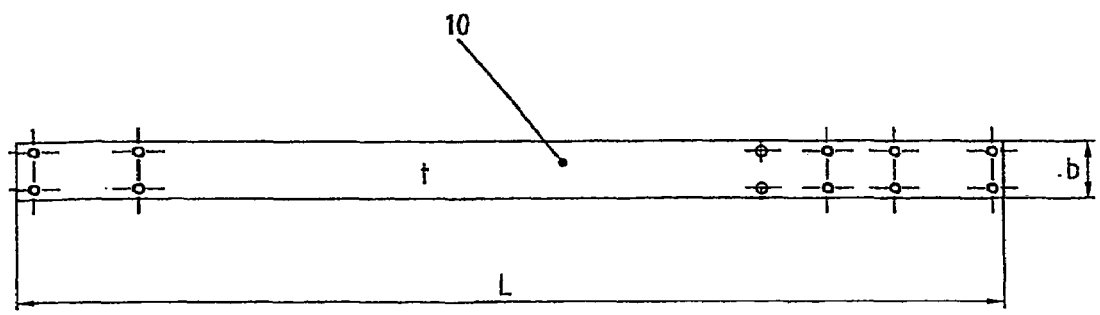
Figure 6:
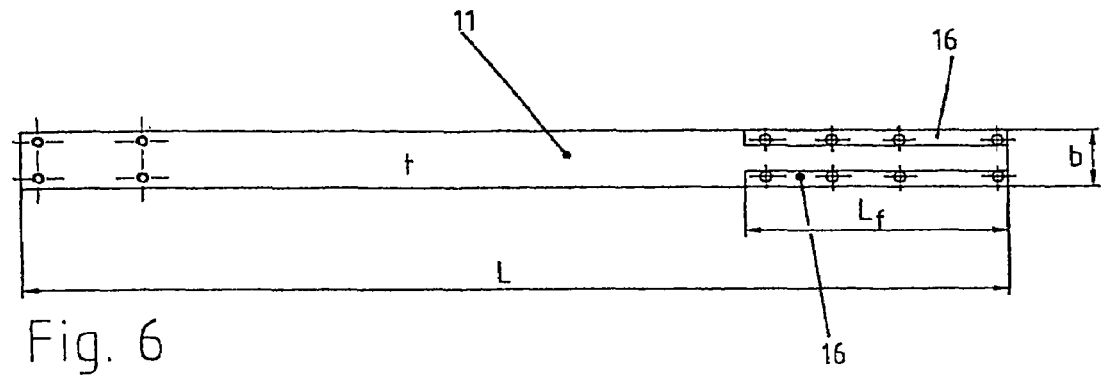
Figure 7:
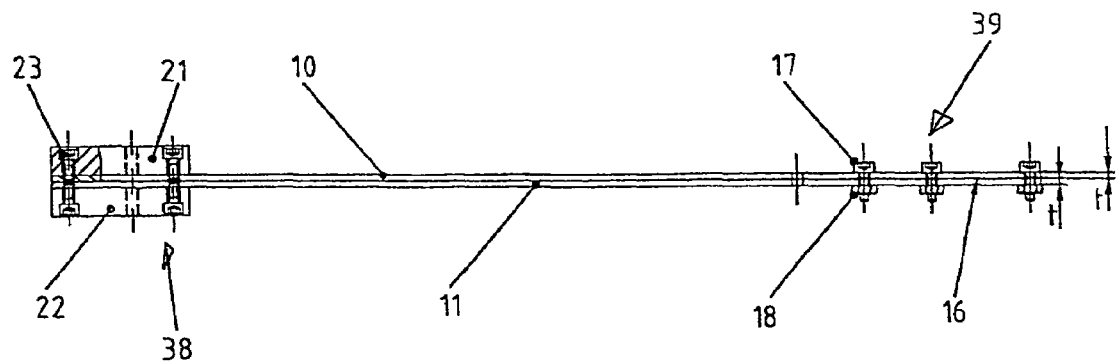
Figure 10:
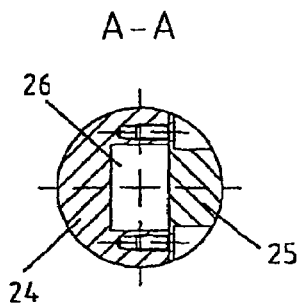
Figure 11:
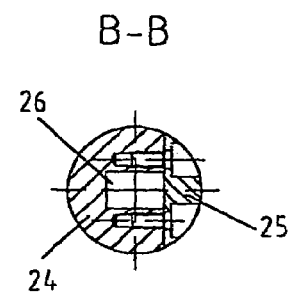
Figure 12:
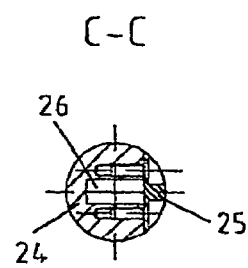
Figure 9:
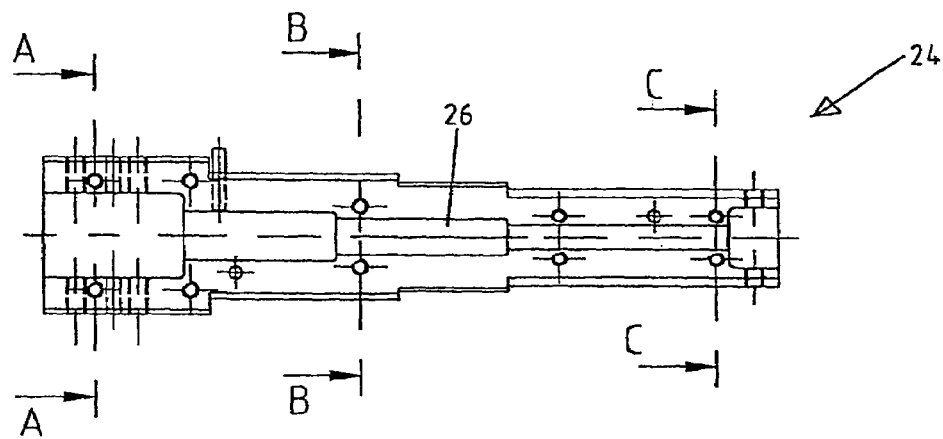
Figure 8:
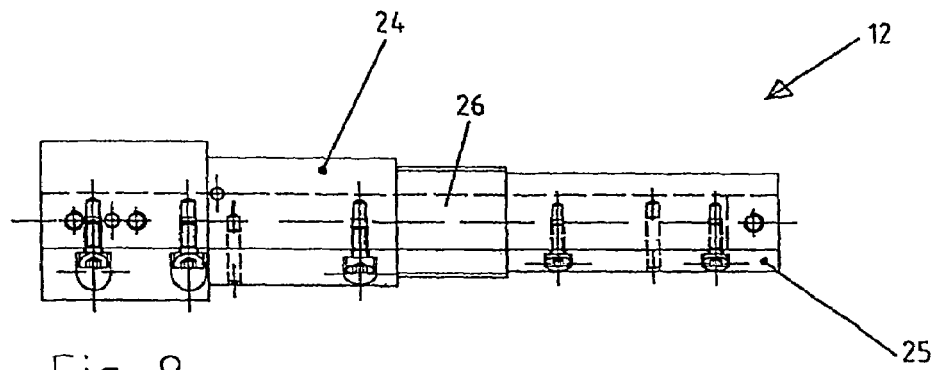
Figure 13:
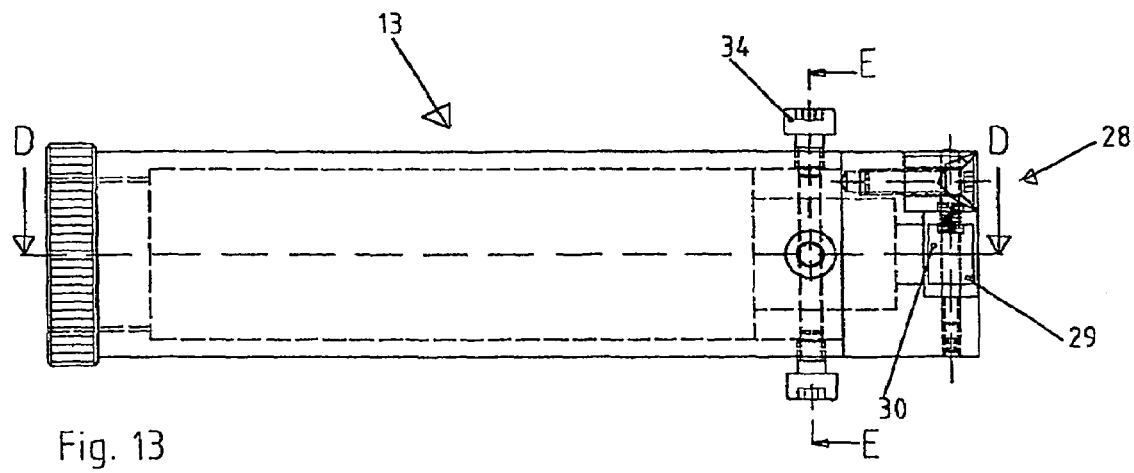
Figure 14:
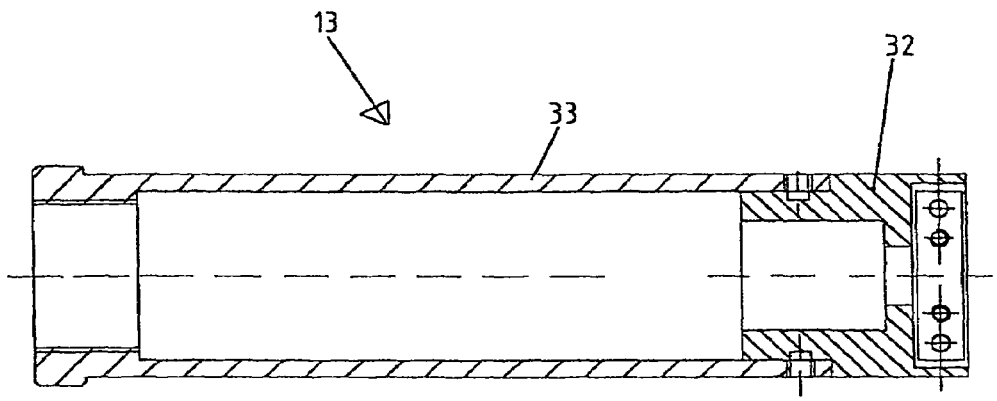
Figure 15:
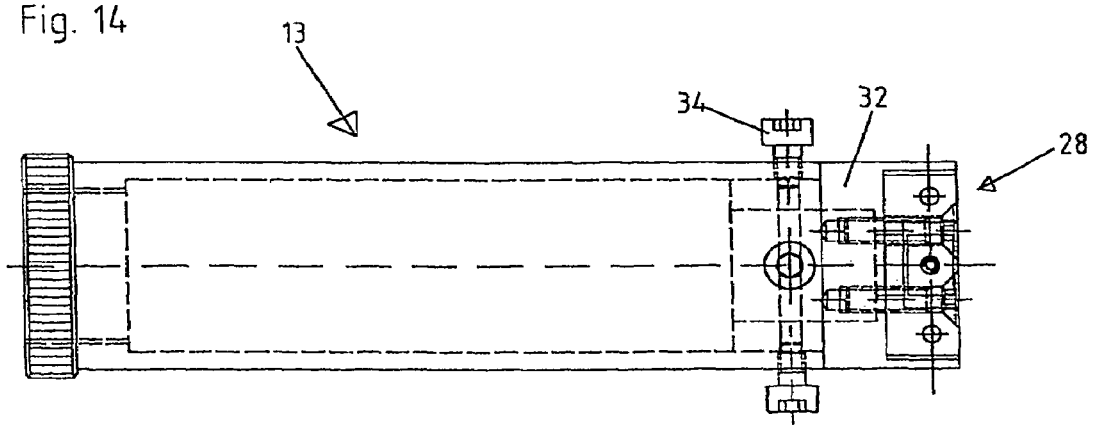
Figure 17:
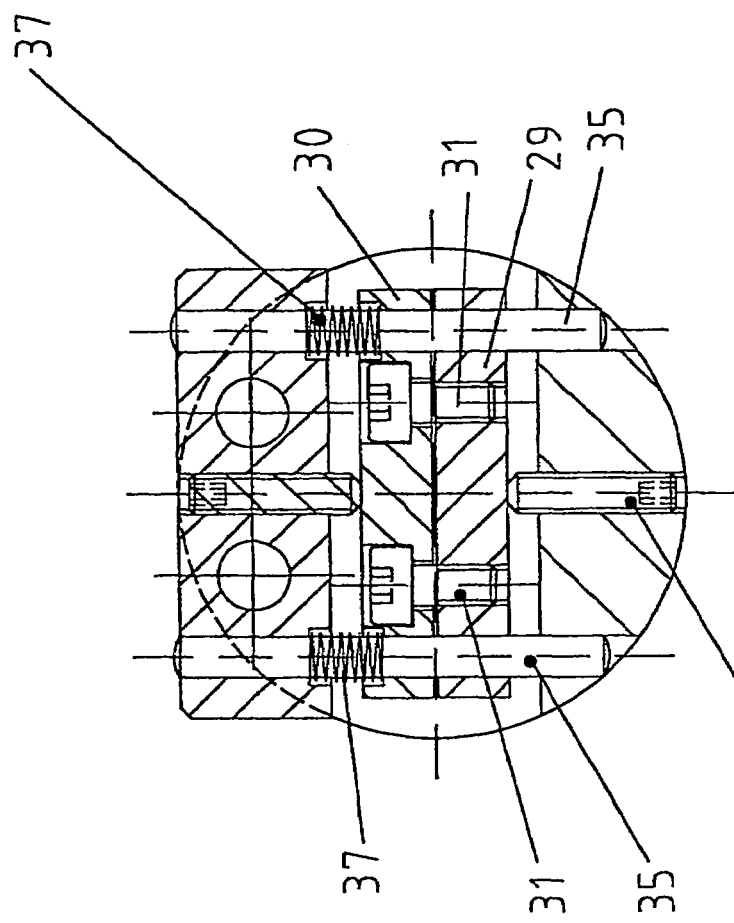
Figure 16:
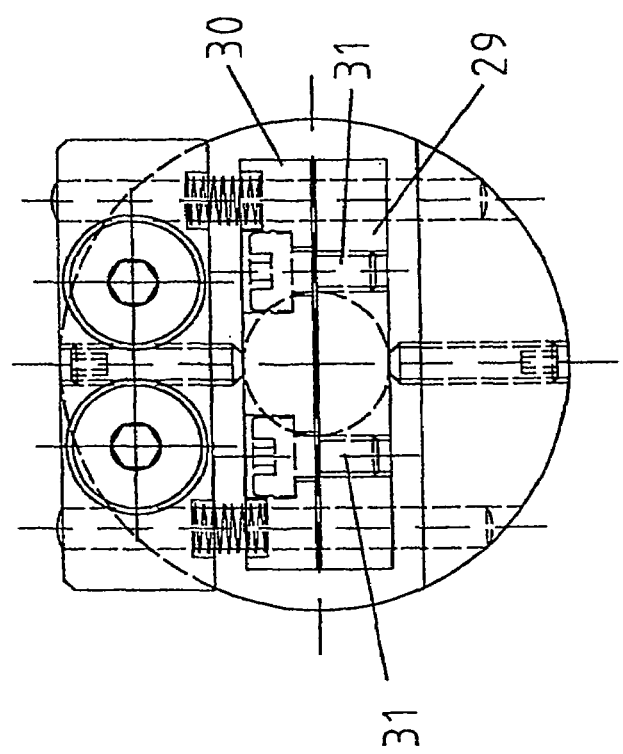
Figure 18:
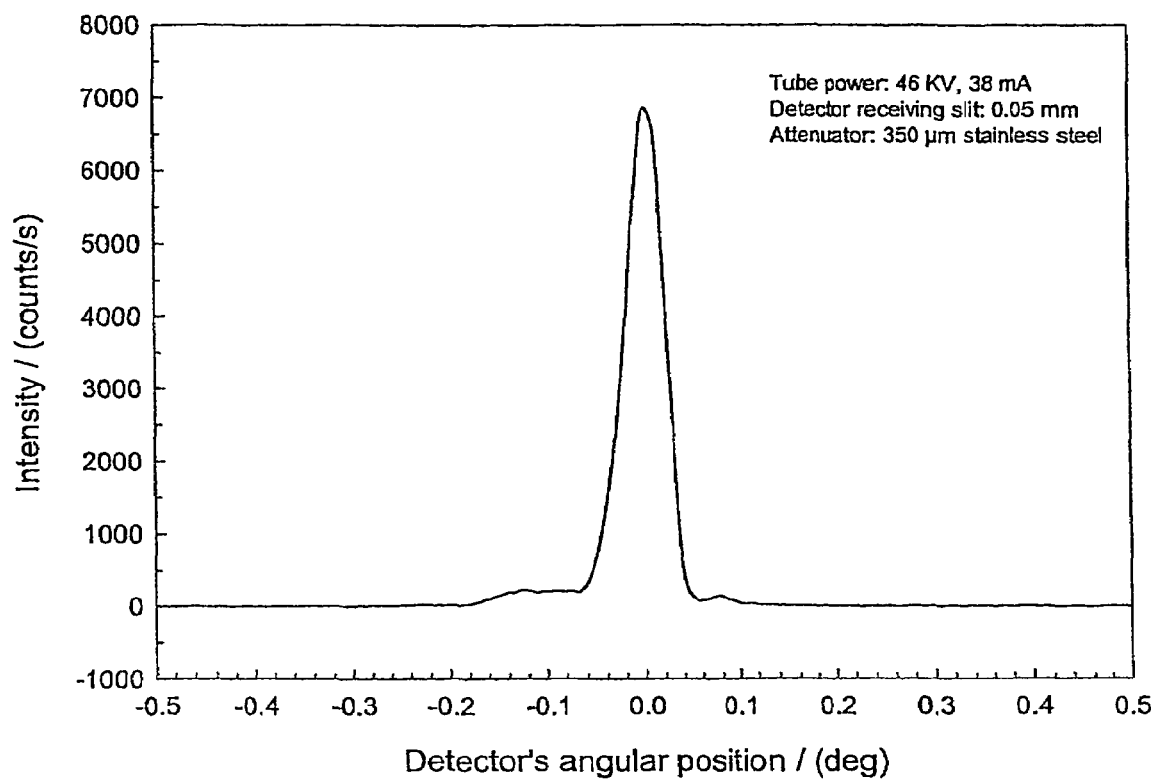
Figure 19:
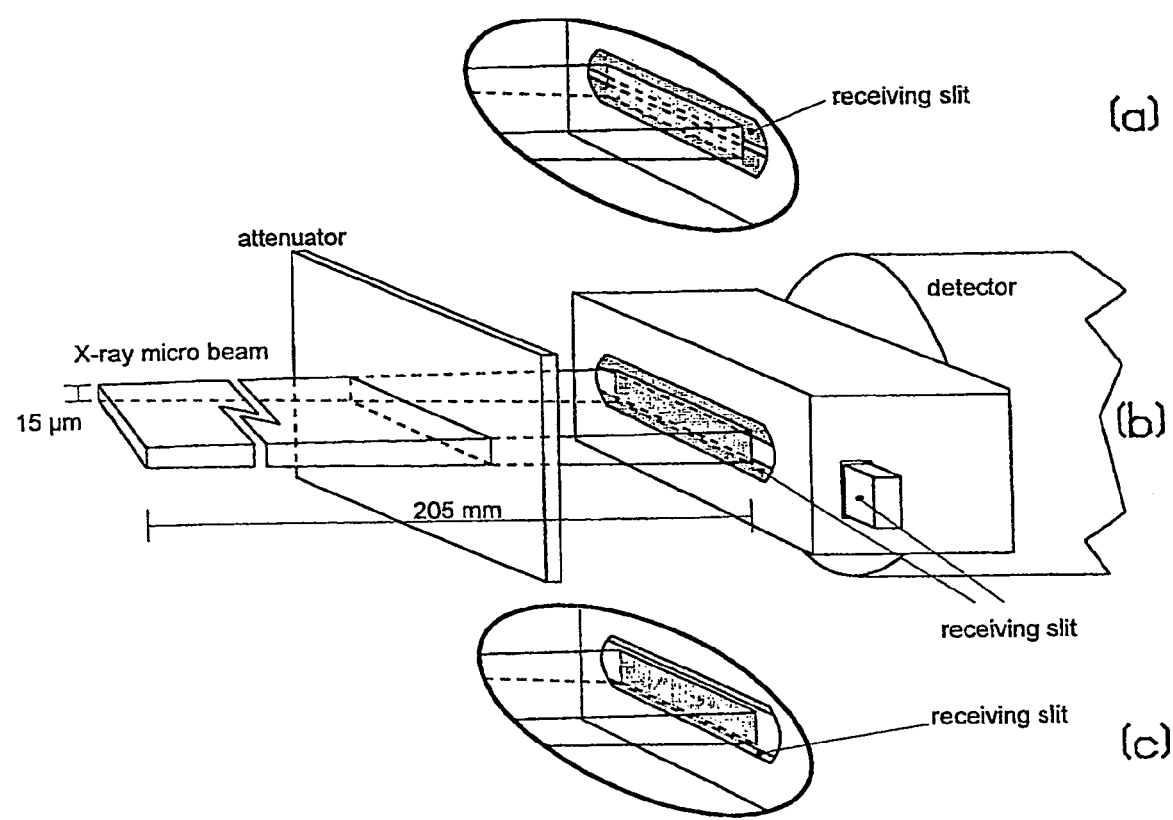
Figure 20:
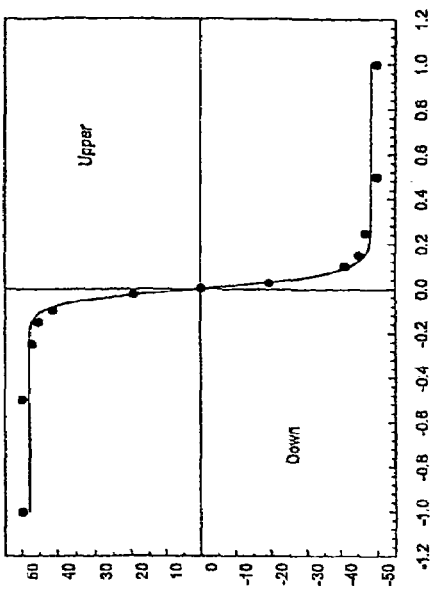
Figure 20:
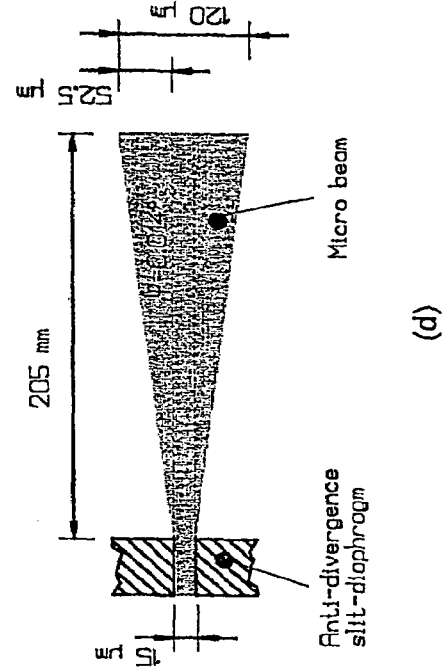
Figure 20:
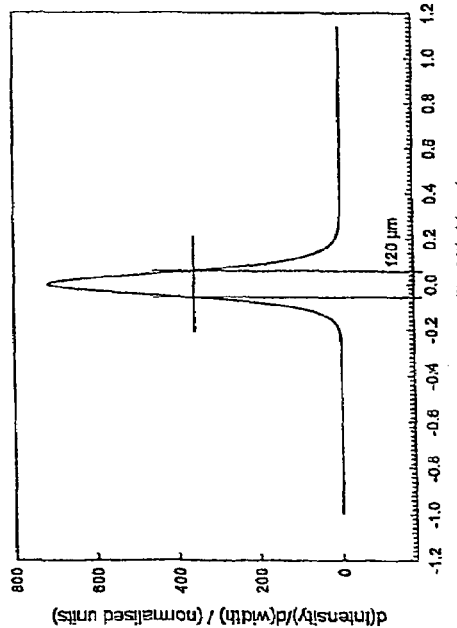
Figure 21:
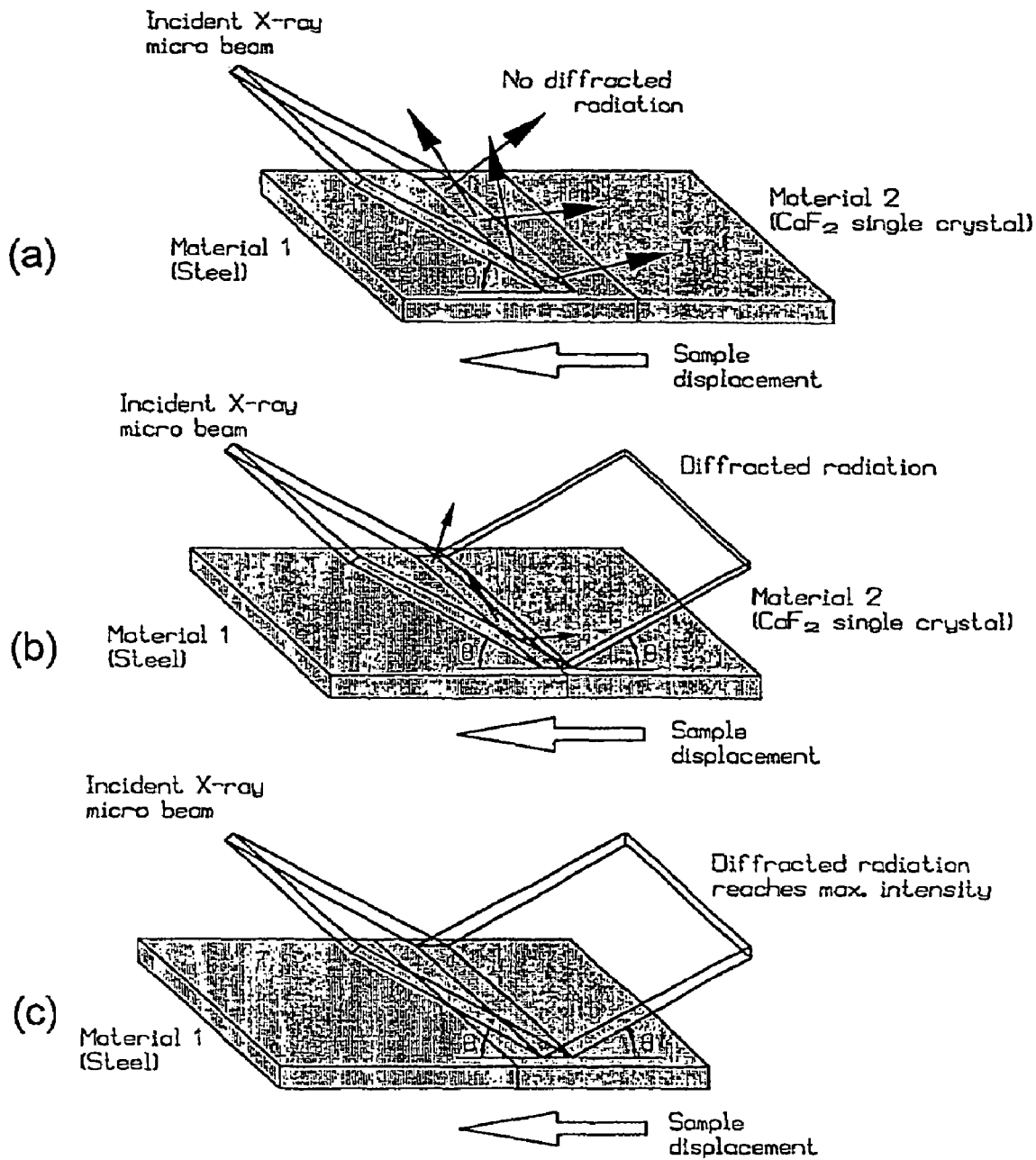
Figure 22:
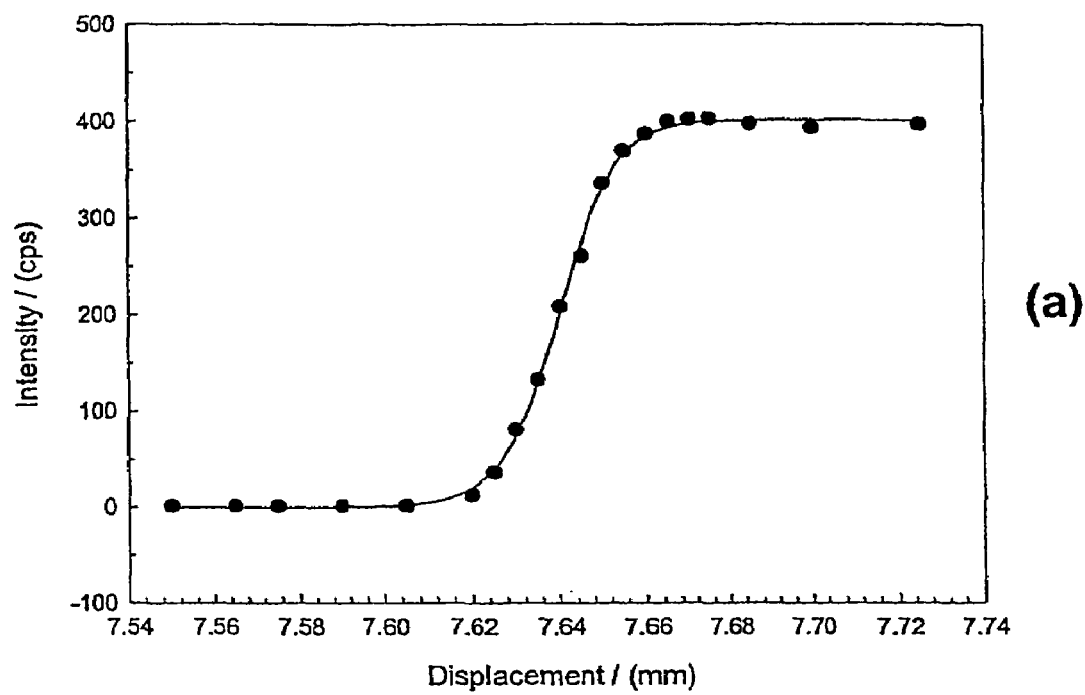
Figure 22:
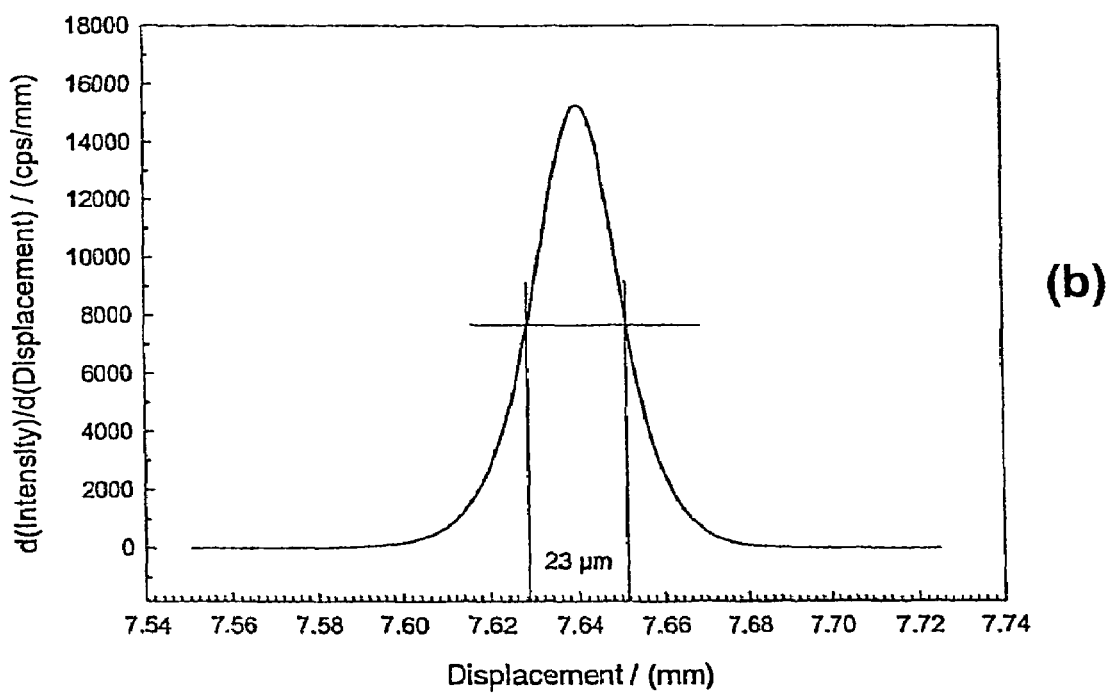
Figure 23:
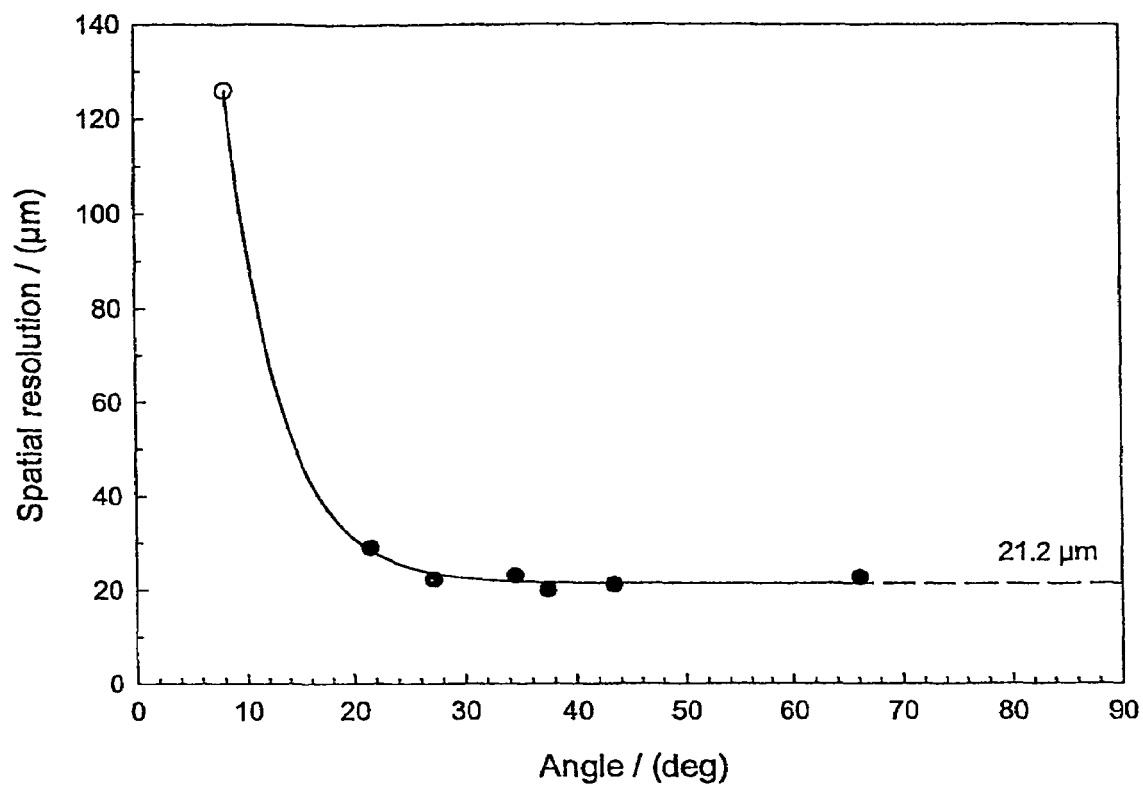
Figure 24:
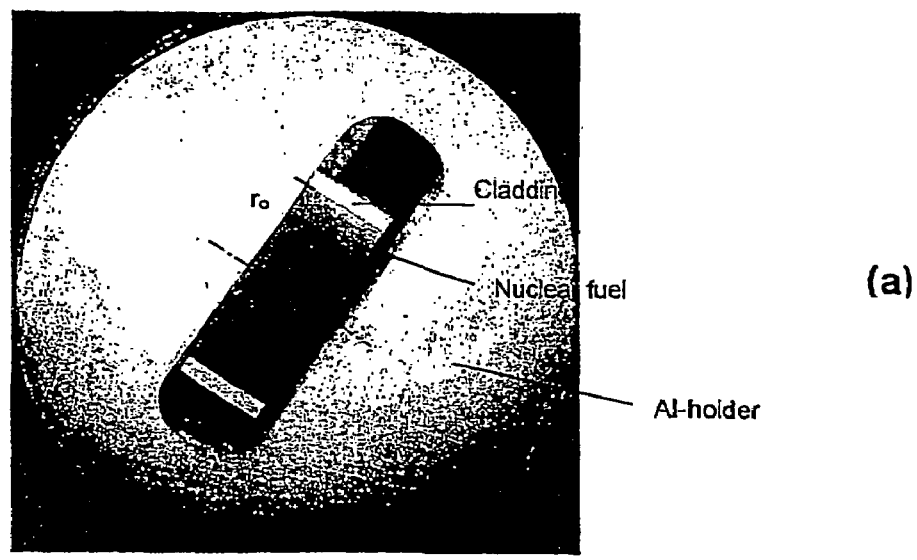
Figure 24:
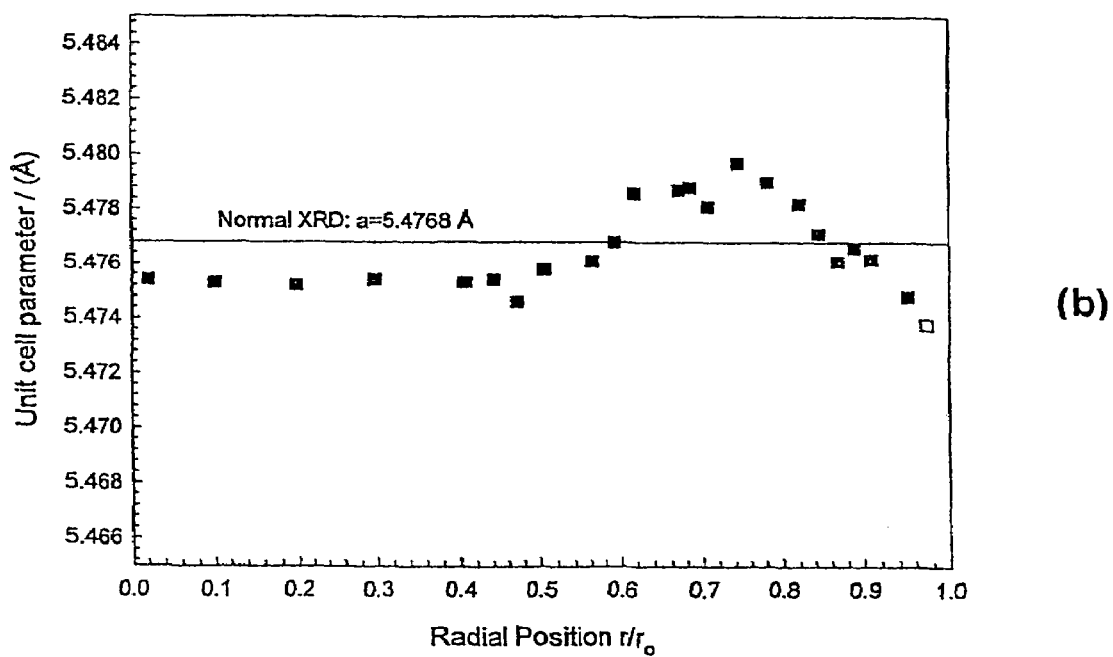

FIG. 5 a top elevational view of the upper plate of the micro beam collimator according to the present invention;

FIG. 6 a top elevational view of the lower plate of the micro beam collimator according to the present invention;

FIG. 7 a side elevational view of the assembled upper and lower plates shown in FIGS. 5 and 6;

FIG. 8 is a top elevational view showing the assembled base part and cover part of the holding means for receiving the two plates;

FIG. 9 is a side elevational view showing the base part of the holding means only;

FIG. 10 the cross sectional view according to line A-A of FIG. 9;

FIG. 11 the cross sectional view according to line B-B of FIG. 9;

FIG. 12 the cross sectional view according to line C-C of FIG. 9;

FIG. 13 is a side elevational view showing the outer housing of the micro beam collimator according to the present invention;

FIG. 14 is a cross sectional view according to line D-D of FIG. 13;

FIG. 15 is a top elevational view of the outer housing shown in FIG. 13;

FIG. 16 is an elevational view of the outer housing seen from the right of FIG. 13;

FIG. 17 is a cross sectional view according to line E-E of FIG. 13;

FIG. 18 is an intensity profile of the generated micro beam as observed by angular detector scanning at 205 mm from the collimator exit tip;

FIG. 19 is an experimental arrangement for estimation of the micro beam divergence. (a)→(c): progressive increase of the receiving slit width and measuring of the transmitted intensity;

FIG. 20 shows the determination of the micro beam's divergence. (a): Intensity transmission (%) to the detector as a function of receiving slit width. (b) Rearrangement of the data assuming total symmetry of the beam, i.e. half of the receiving slit. (c) the $1^{st}$ derivative of the curve, in (b) and beam thickness at FWHM. (d) the divergence angle (0.014°) is determined from the simple geometry of the measuring arrangement;

FIG. 21 shows the determination of the spatial resolution. (a) No diffracted signal is measured by the detector. (b) A part of the beam spot illuminates the $CaF_2$ crystal and the intensity of diffracted radiation is measured by the detector. (c) The diffracted signal reaches maximum intensity;

FIG. 22 shows typical results from the spatial resolution test. (a) Intensity of the diffracted radiation (at incident angle 34.540°) as a function of beam spot location on the interface steel/$CaF_2$. (b) the $1^{st}$ derivative of the curve in (a) and the beam spot thickness at FWHM;

FIG. 23 shows the spatial resolution of the micro beam collimator as a function of beam's incident angle;

FIG. 24 shows an application of the micro XRD apparatus. (a) A close up of a longitudinal cut of a nuclear burnt fuel sample and (b) The observed unit cell (lattice) parameters as a function of radial position of the beam spot on the sample;

FIG. 1 shows the utilised θ/θ-diffractometer with the micro beam collimator 1 of the present invention attached to an radiation tube 2 and a sample-positioning table or micro-positioner 3 that allows precise movements of the sample S with respect to the micro beam B by means of micro screw 4. Further, FIG. 1 shows a scintillation counter or detector 5, a goniometer head and gimbal means comprising a vertical positioner 7, a tilt stage 8 and an angular frame 9.

The whole system shown in FIG. 1 has been used to characterise the beam and to check the technique applicability under realistic operation conditions. Characterisation of the micro beam included intensity gain measurements, as well as beam divergence and spatial resolution tests. Representative XRD observations and lattice parameter measurements were also performed on the longitudinal cut of a nuclear spent fuel pellets and oxidised Zirconium-alloy tubes, demonstrating the capability of the present invention to deliver absolutely resolved (non-overlapping) diffraction spectra of the samples at spatial intervals as low as 30 µm.

Figure 2:
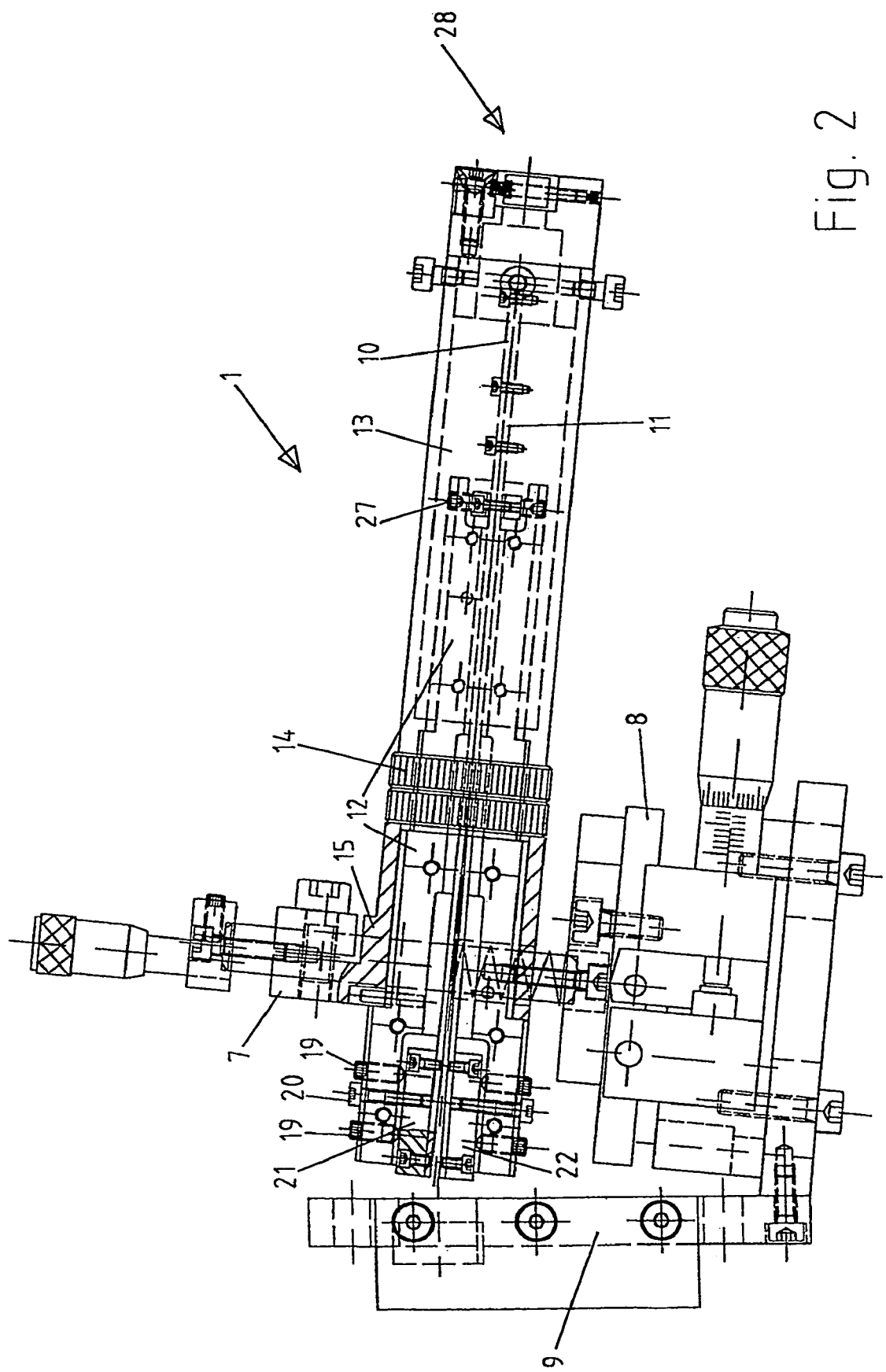
FIG. 2 is a side elevational view showing the micro beam collimator according to the present invention partially in section.

FIG. 2 shows micro beam collimator 1 more detailed. In particular, vertical positioner 7, tilt stage 8 and angular frame 9 constituting the gimbal means are shown. The two plates, upper plate 10 and lower plate 11, forming the channel for guiding micro beam B can be seen. Oblong plates 10, 11 are received in a holding means which is formed by a cylindrical housing 12 preferably made of aluminium. An outer housing or outer tube 13 is threadably connected at 14 to cylindrical housing 12 and partially encloses plates 10, 11 and housing 12. An inner threaded receiving sleeve 15 supports cylindrical housing 12, plates 10, 11 and outer housing 13 of micro beam collimator 1 for connecting it with the gimbal means.

Figure 3:
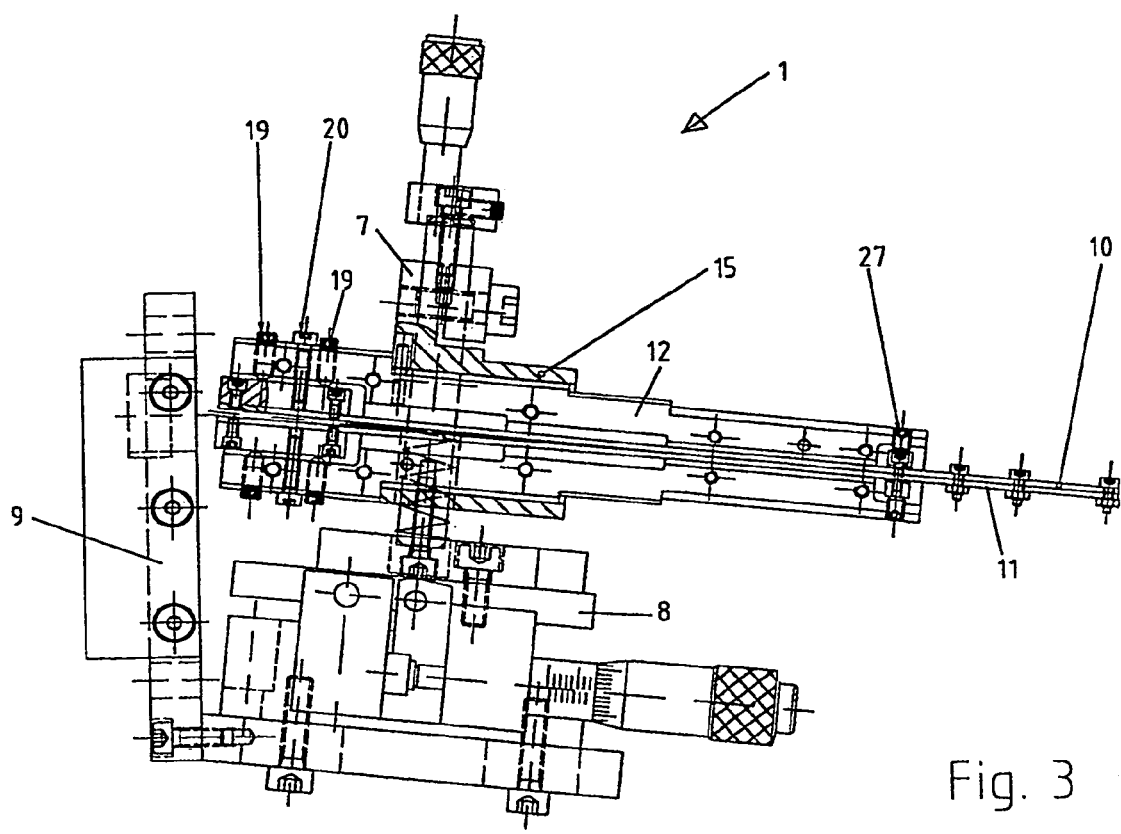
FIG. 3 is a side elevational view showing the micro beam collimator according to the present invention without the outer housing.
Figure 4:
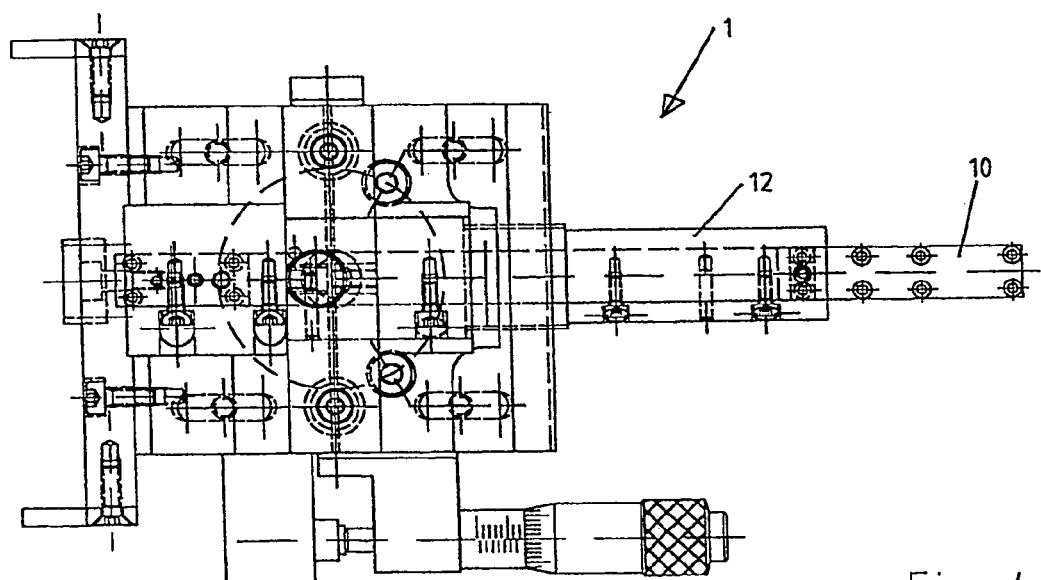
FIG. 4 is a top elevational view of the micro beam collimator shown in FIG. 3.

FIG. 3 shows micro beam collimator 1 without outer housing 13. It can be seen that plates 10, 11 project to the right from housing 12. In FIG. 4 micro beam collimator 1 is shown in a top elevational view.

FIGS. 5, 6 and 7 are showing upper plate 10, lower plate 11 and the assembly comprising plates 10 and 11. In the shown embodiment plates 10, 11 are made of Nickel (Ni). Plates 10, 11 have identical geometry, namely a length of L=150 mm, a width of b=9 mm and a thickness of t=1 mm.

The Ni-Plates 10, 11, one side final-polished with OP-S colloidal silica suspension (grain size 0.04 µm), are positioned with the polished sides to the inside as can be seen in FIG. 7. In the channel exit portion (39), spacer means in the form of two noble metal strip foils 16 of 30 µm thickness are placed between the Ni-plates 10, 11 which are fixed together with a plurality of screws 17 and nuts 18, thereby forming a 37 mm long beam guide of constant cross section of 4 mm×30 µm. Foils 16 of different thickness can be used depending on the required thickness of the generated beam B.

As shown in FIG. 6, the length of strip foils 16 amounts to $L_f$=40 mm leading to a longitudinal extension of the channel exit portion (39) of 37 mm which is defined by the distance between the left most pairs of screws and nuts and the right hand end of plates 10, 11 in FIGS. 5, 6 and 7. Preferably, the channel exit portion (39) having a constant cross section has a length of less than 50%, more preferably of less than 30%, of the total length L of plates 10, 11.

The aperture or opening width at the channel entrance arranged on the left hand side of FIG. 7 is variable. Since the Ni-plates 10, 11 are only 1 mm thick and maintain enough flexibility, their separation at this point can be varied as desired by adjustment or spacer screws 19, 20 as shown in FIGS. 2 and 3, such that adjustments of the entrance (critical) angle can be done until the maximum output intensity is obtained.

On the external side of Ni-plates 10, 11 small bronze blocks 21, 22 are attached by screws 23, as shown in FIG. 7, to facilitate their mounting in the cylindrical housing- or holder means 12 illustrated in particular in FIGS. 2 and 3. Since blocks 21, 22 are fixed to plates 10, 11 respectively and are interacting with spacer screws 19, 20 they form a part of the adjustment means for adjusting the longitudinal profile of the channel and/or the opening width of the channel entrance.

The cylindrical holding means 12 is shown more detailed in FIG. 8 through 12. As shown in FIG. 8, holding means 12 comprises a base part 24 and a cover part 25. The separation plane between base part 24 and cover part 25 is offset from the longitudinal axis of holding means 12, as can be seen in FIGS. 10, 11 and 12. FIG. 9 shows an elevational view of base part 24, wherein the separation plane is identical or parallel with the drawing plane. As best seen in FIGS. 10, 11 and 12 base part 24 has a groove 26 serving as a receiving cavity for receiving Ni-plates 10, 11. After inserting Ni-plates 10, 11 in groove 26 they are held in base part 24 by means of screws 27, 19 and 20 illustrated for example in FIG. 3. Then, base part 24 is closed by cover part 25.

Using screws 19, 20 not only the opening width of the beam channel entrance can be varied, but also the longitudinal profile of the formed oblong channel space between Ni-plates 10, 11. By pressing outer or inner screws 19, either a parabolic (convex) or a tapered (concave) profile can be formed. The radiation compression takes place then between the Ni-plates 10, 11 following multiple total reflections.

The set of Ni-plates 10, 11 and holding means 12 constitutes the condenser unit of the micro beam collimator 1, which is placed between the radiation tube 2 and the sample S. To adjust the position of this unit with respect to the primary beam a gimbal-system that allows combined vertical and tilting movements of the condenser unit is used. This gimbal-system is composed by three elements; namely the vertical positioner 7, the tilt stage 8 and the angular frame 9 as shown in FIGS. 1, 2 and 3. The mounting sequence is as follows: the condenser unit is inserted in the vertical positioner 7, this last is screwed to the top plate of the tilt stage 8, the last is mounted in the angular frame 9 and finally this frame 9 is attached to the X-ray tube housing 2.

The angular frame 9 has already a pre-given angle with respect to the horizontal plane (in the present embodiment −6°), which corresponds to the "take-off" angle of the primary beam according to indications of the X-ray tube provider. The vertical positioner 7 is provided with a micro screw (M-619.00 from PI Physik Instrumente GmbH & Co), which allows vertical displacements of the condenser unit at controllable steps as fine as 10 µm. The tilt stage 8 is a commercial inclinometer of the Type M-041.00, supplied by PI-Physik Instrumente GmbH & Co., Germany. This allows fine variations of the collimator axis orientation around the pre-given take-off angle of the angular frame 9 (−6°), at controllable steps of 0.005°. Once the optimum alignment is achieved, confirmed by collecting the maximum intensity at the collimator exit, both vertical and angular micro-positioners can be locked in their positions by appropriated screws.

An outer tube 13 serving as outer housing is partially enclosing the condenser unit, as shown in FIG. 2. Outer tube 13 is illustrated in FIGS. 13, 14 and 15 more detailed. It has a double function, namely to protect Ni-plates 10, 11 from external physical forces and to support a slit diaphragm 28 serving as anti-divergence means at the output of the micro beam path in order to eliminate the oblique radiation. It is well-known from the glass capillaries that small imperfections in the inner reflecting walls or slight misalignments of the entrance opening with respect to the primary beam cause significant intensity variations within the concentrated beams, such as helical or other noncentrosymmetric features [see prior art reference 8] and produce disturbing divergent beams (satellites). In the present invention, to cut the disturbing the oblique radiation and to keep only the central core of the concentrated beam, a 15 µm anti-divergence slit is located in the front of the exit aperture of the condenser unit.

The slit diaphragm 28 (beam stopper) comprises two blocks 29 and 30, with polished surfaces (up to 0.04 µm roughness) at the inside of the beam, which are fixed together by screws 31 and are attached to an end cap 32 forming a part of outer housing 13, as shown in FIGS. 13, 16 and 17. The round end cap 32 carrying the slit diaphragm 28 is inserted in the front of a protective tube 33, being possible to lock it by tightening screws 34 after setting the slit-aperture parallel to the Ni-plate aperture.

To form the desired slit-aperture, two spacer-rings preferably in the form of foils are laid around screws 31 and thus between blocks 29 and 30. The thickness of the spacer-rings is about 15 µm. Consequently, the slit diaphragm aperture is half of the aperture of the Ni-plates 10, 11 in the channel exit portion 39. To set slit diaphragm 28 at the middle plane of micro beam B, up and down movements of blocks 29 and 30 on two pins 35 can be done by turning screw 36 against the action of springs 37, as is best shown in FIG. 17.

Now, experimental data with respect to the present invention will be presented:

1. Instrumentation

The apparatus which is shown in FIG. 1 has been employed to characterise and to test the micro beam B of this invention. It consists of a θ/θ mode diffractometer (Seifert XRD-3000) equipped with a standard 2 KW radiation tube with line focus Cu anode and a double collimated (i.e. with anti-scatter and receiving slits) scintillation counter (Seifert SZ 20/SE). A Ni filter placed on the tube housing is utilised to eliminate the Cu—$K_\beta$ wavelengths, permitting only Cu—$K_\alpha$ (8.05 keV) to be guided into the collimator. For all experiments the applied power to the radiation tube was 46 KV and 38 mA.

The X-ray micro beam collimator 1 is mounted on the radiation tube housing 2. Keeping both the radiation source and detector arms at the goniometer's zero position, the condenser is oriented into the primary beam path, searching for the maximum transmitted intensity by movements of the vertical and tilt micro-positioning systems. The intensity profile of the formed micro beam B is then scanned by oscillating the scintillation counter around the zero-position. For such direct measurements the scintillation-counter must be protected by an intensity-attenuator to avoid its overflow. This is usually achieved by placing several metallic foils in the front of the detector, some tens or hundreds micrometer thick depending on the incoming intensity. During the alignment, also the angular and vertical positions of the anti-divergence slit at the end of the protective tube (33) are optimised. Furthermore, the entrance opening of the Ni-plates and the profile of the channel enclosed by them are adjusted by using the screws (19) and (20), so as to obtain the maximum transmitted intensity.

2. Intensity Gain and Operational Characteristics

The brilliance win has been determined by measuring the intensity that is emerged from the collimator with and without having inside the Ni-plates, i.e., with and without beam compression. Both measurements have been done under the same experimental conditions, i.e., maintaining the generator parameters constant and after adjustment of the system for maximum transmitted intensity at the goniometer zero position, with a thickness of 50 µm stainless steel foils as intensity-attenuator in the front of the detector. Under these conditions, the arrangement with Ni-plates gave an intensity of $4 \times 10^4$ counts/s, whereas without the Ni-plates the maximum intensity did not exceed $2 \times 10^2$ counts/s. Doubtless, the 200 times higher intensity attained with the Ni-plates verifies the efficiency of the presented beam-compression system, which is utilisable for hard X-rays in the range 5-30 keV. For comparison, glass mono-capillary concentrators operated with conventional Cu $K_\alpha$ radiation sources reached only a gain of intensity of about 28 [see prior art references 7].

The intensity profile measured at a distance of 205 mm from the exit of the collimator, with 350 µm stainless steel foils in front of the detector, is shown in FIG. 18 as a function of the departure of the detector from the angular zero position. It can be seen that the here presented system provides a very well defined and compact X-ray beam (needle form), without significant disturbing "satellite" peaks or increased background radiation. Due to the narrow and pure beam-profile, not only the instrument centre (zero) position can be defined therefore very precisely (a known handicap of the glass-capillary concentrated beams is the diffuse zero position [see prior art references 8]), but also the obtained Bragg peaks from studied samples are free of deformations and very narrow. This contributes also to obtain very precise lattice parameter measurements.

Compared to glass-capillary constructions, the presented concentrator exhibits also some additional advantages. For instance, the intensity of the generated beam during operation is constant, being showed that the system is not sensible to heating effects, which in the case of glass capillaries influence negatively the throughput and disturb the transmitted signal [see prior art references 7]. Also, since our concentrator is made of metal, with a larger absorption coefficient, there is practically no radiation "leakage" through the reflecting walls as in the case of glass-capillaries [see prior art references 2]. Finally, radiation damages in the reflecting Ni-plates have not been detected after several months of continuous operation, different to glass-capillares that show darkening of the walls after a certain time [see prior art references 7], which could affect the efficiency and decrease the reflecting power.

3. Beam Divergence

In the arrangement shown in FIG. 1, the distance between the anti-divergence slit at the collimator exit and receiving slit at the detector, when both radiation source and detector are brought to zero position, is fixed at 205 mm. A simple measurement has been therefore conducted to estimate the beam divergence, by placing different receiving slits of increasing apertures (FIG. 19), until a saturating maximum intensity was recorded. Clearly, a saturating maximum value of transmitted intensity is achieved when the width of the receiving slit exceeds the width of the beam at the intersection place, i.e. after the entire beam enters the detector window. The results of the measured intensities as a function of the receiving slit widths are shown in FIG. 20a. In FIG. 20b the same results are represented assuming total symmetry of the beam, i.e. half of the beam intensity is assumed to pass through half of the receiving slit. The $1^{st}$ derivative of the curve of FIG. 20b is shown in FIG. 20c. Similarly as in references [see prior art references 2,8], a characteristic width is assigned to the micro-beam as the "full width at half maximum" (FWHM) of the peak in FIG. 4c, which implies a width of 120 µm of the beam at a distance of 205 mm from the anti-divergence slit. From simple geometry it can be easily calculated that the corresponding angular divergence is only 0.014°. This value, certainly quite lower than the 0.32° measured for glass mono-capillary concentrators under similar conditions [see prior art references 7,8], indicates the high compactness of the here presented micro beam.

It should be noted also that the given value of 0.014° is the highest possible angular divergence in our case. This is because any misalignment of the receiving slit position from the ideal plane perpendicular to the beam axis leads to the measurement of higher divergence angles than the real. Since in the measurements described before no optimisation of the receiving slit position was done, the derived angular dependence implies therefore a conservative (high) limit value.

The low beam divergence implies another advantage of the presented system with respect to the glass capillaries, since it allows the micro-beam device to be placed at higher distances from the sample surface without sensible loss of spatial resolution. In the following spatial resolution test, certainly confirming the high compactness of the formed beam, the collimator exit is placed at the comfortable distance of 17 mm from the sample, which facilitates the whole experimental handling. As a comparison, conditioned by the larger beam divergence, similar measurements with glass capillaries are done with the exit of the capillary almost in contact with the sample [see prior art reference 8], i.e. at a distance of 2 mm or less from the sample surface.

4. Spatial Resolution

The spatial resolution of the micro beam collimator has been determined experimentally under the same operating conditions of routine measurements with the diffractometer of FIG. 1. For this purpose, a specific sample has been prepared, consisting of a junction of two different materials, a stainless steel plate and a $CaF_2$ single crystal which were fixed together forming a well-defined straight interface edge. The examinations were done on the specimen after fine polishing, placing it on the translation stage (M-105.10 PI Physik Instrumente GmbH & Co.) of the sample positioning system. The measuring procedure is described schematically in FIG. 21; the goniometer arms were located at a certain pre-selected angle $\theta$ with respect to the sample surface, such that a diffracted peak for the $CaF_2$ single crystal was obtained. The beam spot was then positioned initially on the stainless steel plate and the sample was carefully displaced horizontally at 5 μm steps. The illuminated zone thickness (spot size) was then evaluated from the total sample displacement needed, so that the diffracted intensity varied from the background level to a maximum. (It is only to be remarked that because the prepared sample surface was not perfectly parallel to the growth-plane of the $CaF_2$ crystal used, the measured diffraction angles $\theta$ did correspond exactly to be tabulated Bragg-angles for $CaF_2$)

A representative result obtained with the micro beam positioned at an incident angle $\theta=34.540°$ is given in FIG. 22($a$). By differentiation of the curve intensity vs. displacement of FIG. 22($a$), the spatial resolution was defined as the displacement interval corresponding to the full width of half maximum (FWHM) of the peak shown in FIG. 22 ($b$). Such intensity profiles were then obtained for all incident angles $\theta$ leading to diffracted peaks of the $CaF_2$ crystal, being the measured spatial resolutions plotted as a function of the incident angle as represented in FIG. 23.

The exponential decrease of the spatial resolution follows the expected dependence of the beam width projection on the sample surface with the incident angle, which is equal to the cross-section beam width divided by $\sin \theta$. Obviously, at $\theta=0$ the projected width becomes infinite large, while at the extrapolation to $\theta=90°$ it approaches the cross-sectional beam width, which in our case is 21.2 μm (FIG. 23).

The beam width as a function of distance from the collimator tip can be of course calculated by the known divergence angle (0.014°). Taking into account that the anti-divergence slit aperture is 15 μm and that in the chosen configuration it is positioned 17 mm from the sample surface, the cross-sectional beam width in μm is $15+2\cdot17\times10^3\cdot\tan(0.014°)=23.3$ μm. The resulted value is in very good agreement with the experimentally obtained (21.2 μm) and confirms once more the high compactness of the created micro beam.

5. High Resolution XRD Investigations

The XRD apparatus of FIG. 1 equipped with the micro beam collimator and the sample micro-positioning stage has been used to carry out high resolution crystallographic investigations on the nuclear spent fuel specimen of FIG. 24($a$). The sample, a longitudinal cut in the middle of small segment (disk) of a fuel pin, was positioned on the translation stage of the goniometer. By displacing it horizontally, a series of XRD spectra were obtained at several positions on the sample surface. The unit cell constant (parameter) calculated from each individual XRD spectrum is given in FIG. 24 ($b$) as a function of relative radial position ($r/r_0$) of the beam spot on the sample surface. In the same graph is also shown the average unit cell parameter (a=5.4768 Å) as observed using the conventional collimator, which illuminated the whole sample surface. More about the physical meaning of the structural changes among the radius of the examined sample can be found shortly in ref. [see prior art references 10]. The results of FIG. 24($b$) are presented in this section as an example of important high resolution XRD results obtained using the X-ray micro beam concentrator.

As is evident from the above description the present invention provides the following advantages:

Stable construction against physical external forces.
Higher construction lengths allowing larger entrance openings for capturing most radiation available for compression.
No radiation leakage through the condenser, walls due to the high density of the Ni-material.
No heating effects affecting the transmitted intensity.
High stability against radiation damages.
Exit flat channel of constant cross-section providing quasi-parallel output beam.
Variable nominal output width of the formed beam using different spacer foils between the plates of controllable thickness.
Variable cross-section profile of the channel formed between the Ni-plates with tapered or parabolic configurations for maximum transmitted intensity.
Variable slit width by using different spacer foils, slightly lower than the output width of the metallic channel in the X-ray condenser.
Absorption of most divergent and disturbing radiation and final formation of a low divergent micro beam with narrow-compact intensity profile.
Precise definition of the system zero position due to high compactness of the beam.
Due to compactness of the incident beam, very thin and well defined diffracted beams (peaks) allowing high precision crystallographic determinations.
Due to the low divergence of the formed beam, comfortable distance between the collimator tip and the sample, at least 17 mm, without loss of spatial resolution.
Due to the high spatial resolution, possibility of obtaining precise non-overlapping diffraction spectra of the samples at intervals slightly larger than 20 μm.

PRIOR ART REFERENCES

1. D. Bilderback, S. A. Hoffman and D. Thiel, Science, 263, (1994).
2. Naoki Yamamoto, Rev. Sci. Instrum., 67 (9), (1996).
3. P. Dhez, P. Chevallier, T. B. Lucatorto and C. Tarrio, Rev. Sci. Instrum., 70, (4), (1999).
4. D. H. Bilderback, D. J. Thiel, Rev. Sci. Instrum., 66 (2), 1995).
5. H. Klug and L. Alexander, "X-ray diffraction procedures", John. Wiley & Sons, Inc., New York (1954).
6. A. H. Compton and S. K. Allison, "X-rays in Theory and Experiment", D. Van Nostrand Company, Inc., (1935).
7. D. J. Thiel, D. H. Bilderback and A. Lewis, Rev. Sci. Instrum., 64 (10), (1993).
8. I. C. Noyan, P.-C. Wang, S. K. Kaldor, J. L. Jordan-Sweet and E. G. Liniger, Rev. Sci. Instrumen., 71 (5), (2000).
9. C. A. MacDonald, S. M. Owens and W. M. Gibson, J. Appl. Cryst., 32, 160-167, (1999).

The invention claimed is:

1. A micro beam collimator for compressing X-ray beams for use in a X-ray diffractometer, said collimator comprising:
a channel means formed by two opposite, polished oblong flexible plate means for providing a channel guiding said X-ray beams and said channel means having a channel entrance and an exit portion;
said plate means made of or coated with a material selected from the group consisting of the heavyweight metals and materials having total reflection properties comparable to those of the heavyweight metals; and
adjustment means provided for adjusting a longitudinal profile of said channel and/or the opening width of said channel entrance portion by bending said plate means.

2. A micro beam collimator according to claim 1 wherein said group consists of nickel, wolfram and platinum.

3. A micro beam collimator according to claim 1 wherein said channel has a constant cross-section in said channel exit portion so that a quasi-parallel output X-ray beam is produced.

4. A micro beam collimator according to claim 1 wherein said channel exit portion has a length of less than 50% of the total length (L) of said channel.

5. A micro beam collimator according to claim 1 wherein said channel exit portion has a length less than 30% of the total length (L) of said channel.

6. A micro beam collimator according to claim 1 wherein spacer means are sandwiched in said channel exit portion between said plate means for spacing the same.

7. A micro beam collimator according to claim 6 wherein said spacer means are two noble metal strip foils.

8. A micro beam collimator according to claim 1 wherein said plate means are received in a holding means having a receiving cavity.

9. A micro beam collimator according to claim 8 wherein said receiving cavity has a width increasing in the direction from said channel exit portion to said channel entrance portion.

10. A micro beam collimator according to claim 8 wherein an outer housing means connectable to said holding means is provided for at least partially enclosing said plate means and said holding means.

11. A micro beam collimator according to claim 1 wherein said adjustment means includes two block means each of which being fixed in said channel entrance portion to the outside of each of said plate means; and
a plurality of adjustment screws mounted in holding means and interacting with said block means.

12. A micro beam collimator according to claim 1 wherein anti-divergence means is located at said channel exit for stopping oblique radiation.

13. A micro beam collimator according to claim 12 wherein said anti-divergence means is mounted in an end portion of an outer housing means.

14. A micro beam collimator according to claim 13 wherein said end portion is formed by an end cap detachably connectable to the remaining part of said outer housing means.

15. A micro beam collimator according to claim 12 wherein said anti-divergence means includes two diaphragm blocks forming a slit between each other.

16. A micro beam collimator according to claim 15 wherein further spacer means are arranged between said diaphragm blocks for adjusting the width of said slit.

17. A micro beam collimator according to claim 15 wherein aligning means are provided for aligning said slit with said channel exit portion.

18. A method of carrying out high resolution XRD studies, said method comprising the following:
using a micro beam collimator for compressing X-ray beams for use in a X-ray diffractometer having a channel means formed by two opposite, polished oblong flexible plate means for providing a channel guiding said X-ray beams and said channel means having a channel entrance and exit portion, said plate means made of or coated with a material selected from the group consisting of the heavyweight metals and materials having total reflection properties comparable to those of the heavyweight metals; and
adjusting by adjustment means a longitudinal profile of said channel and/or the opening width of said channel entrance portion by bending the said plate means; and
a diffractometer equipped with a micropositioning means for positioning a sample to be scanned.

19. A micro beam collimator for compressing X-ray beams for use in a X-ray diffractometer, said collimator comprising:
a channel means formed by two opposite, polished oblong plate means for providing a channel guiding said X-ray beams and said channel means having a channel entrance and an exit portion, said plate means being made of or coated with a material selected from the group consisting of the heavyweight metals and materials having total reflection properties comparable to those of the heavyweight metals, said plate means forming an aperture in said channel exit portion; and
an anti-divergence means located at the channel exit portion for stopping oblique radiation, said anti-divergence means including two diaphragm blocks forming a slit between each other, said slit being parallel to said aperture in said channel exit portion.

20. A micro beam collimator according to claim 16 wherein aligning means are provided for aligning said slit with said channel exit portion.

* * * * *